US008632478B2

(12) United States Patent
Alkhattaf

(10) Patent No.: US 8,632,478 B2
(45) Date of Patent: Jan. 21, 2014

(54) PILLOW WITH MECHANISM FOR SIMULATED RESPIRATION

(76) Inventor: Solaiman B. Alkhattaf, Qadsia (KW)

(*) Notice: Subject to any disclaimer, the term of this patent is extended or adjusted under 35 U.S.C. 154(b) by 765 days.

(21) Appl. No.: 12/773,123

(22) Filed: May 4, 2010

(65) Prior Publication Data

US 2011/0275966 A1 Nov. 10, 2011

(51) Int. Cl.
*A61H 1/00* (2006.01)
*A61H 9/00* (2006.01)

(52) U.S. Cl.
USPC ........... 601/15; 601/56; 601/64; 601/148; 5/644

(58) Field of Classification Search
USPC ........... 601/15, 39, 46, 49, 55, 56–59, 60, 61, 601/64, 65, 67, 69, 70, 75, 76, 78, 84, 88, 601/96, 105, 107, 108, 111, 134, 136, 138, 601/145–150; 5/421, 633, 636, 639, 644, 5/655.3, 655.5, 915, 933
See application file for complete search history.

(56) References Cited

U.S. PATENT DOCUMENTS

| 2,800,897 | A | | 7/1957 | Ross |
| 2,850,009 | A | | 9/1958 | McElwee |
| 3,981,032 | A | | 9/1976 | Brooks |
| 5,503,618 | A | | 4/1996 | Rey |
| 5,771,514 | A | * | 6/1998 | Wilhoit ........................... 5/644 |
| 6,175,981 | B1 | | 1/2001 | Lizama |
| 6,256,818 | B1 | * | 7/2001 | Hughes ........................... 5/639 |
| 7,988,649 | B1 | * | 8/2011 | Kost ............................... 601/15 |
| 2004/0193078 | A1 | * | 9/2004 | Flick et al. ..................... 601/58 |

* cited by examiner

*Primary Examiner* — Quang D Thanh
(74) *Attorney, Agent, or Firm* — Lowe Hauptman & Ham, LLP

(57) ABSTRACT

A pillow with simulated respiration includes a pair of impervious panels that are joined together to form a rectangular shaped enclosed body and a mechanism for inflating/deflating the body periodically to simulate an individual's breathing. The pillow may also include a cushion on top of the body with an electric heating pad on top of the cushion together with a pair of vibrators. The vibrators each have an elongated shape and are constructed and dimensioned to message an individual's neck and upper shoulders when the individual's head is placed on the cushion. The pillow also includes a textile cover with a zipper on one side thereof and a satin pillow case.

1 Claim, 2 Drawing Sheets

PILLOW WITH MECHANISM FOR SIMULATED RESPIRATION

FIELD OF THE INVENTION

This invention relates to pillow with a mechanism for simulating respiration and more particularly to a pillow for relieving stress and relaxing an individual and relieving the effects of fatigue and pain in the neck and/or shoulder area.

BACKGROUND OF THE INVENTION

Heated massage pillows are well known and have been in use for many years. For example, a U.S. Pat. No. 2,800,897 of Ross discloses a pillow with vibratory and heating means. The patent discloses a vibrating means that includes a motor resiliently mounted within a housing and including a shaft with an eccentric weight mounted on the shaft.

A more recent U.S. Pat. No. 5,771,514 of Wilhoit discloses an adjustable contour pillow that provides for manual and/or powered inflation of the chamber or chambers therein as well as other alternative features such as heat, message and/or cooling and is useful to persons suffering from neck strain. In one embodiment, the pillow includes three separate laterally disposed elongate fluid chambers, each having a coplanar lower wall. The central chamber has a center and an upper wall which is lower than the centers and upper walls of the other two chambers, thus defines an elongate valley extending from one end to the other of the pillow. The valley serves to cradle the back of the head with the uppermost chamber (relative to the user) cradling the upper back of the head and the lowermost chamber supporting the back of the neck of a supine person. The selective and independent inflation of the different chambers may be accomplished manually, or by an automated powered pump arrangement. The control system may be integrated with the pillow, or may alternatively be supplied as a separate control for a pillow having one or more inflatable chambers therein.

A further approach to message pillows is disclosed in a U.S. Pat. No. 6,256,818 of Hughes. As disclosed in the Hughes patent, the heated massage pillow allows the message packs to be removed and for keeping hair looking nice. The heated message pillow includes a pillow comprised of a first pillow case and a foam rubber cushion. The foam rubber contains a heating means. A power supply means is adapted to fit inside the first pillow case adjacent to the foam rubber and is operationally coupled to the heating means. Vibrating means are adapted to fit inside the first pillow case adjacent to the power supply. The vibrating means are operationally coupled to the power supply means. An actuating means, located outside of the first pillow, is operationally attached to the vibrating means. The actuating means is adapted to activate the vibrating means and the heating means. A second pillow case of satin is adapted to fit over the first pillow case.

Notwithstanding the above, it is presently believed that there is a need and a potential commercial market for an improved pillow with a mechanism for simulating breathing in accordance with the present invention. There should be a need and a potential commercial market for an improved pillow that alleviates fatigue and pain in the neck attributed to excessive exertion and/or poor sleeping positions. Further, it is believed that the simulated response will relieve stress and relax an individual.

BRIEF SUMMARY OF THE INVENTION

In essence the present invention contemplates a pillow with a mechanism for simulating respiration. The respiration simulating mechanism may include means to control the inflation and deflation of a bellows and to do so to match the breathing of the individual. The pillow in accordance with the present invention may also include vibrating means for relieving stress in the neck and upper shoulders of the individual as well as means for heating the pillow to apply heat and vibration simultaneously with the simulated respiration.

A preferred embodiment of the invention contemplates a pair of relatively impervious panels having two elongated sides and two short sides joined together to form an enclosed body, together with means for inflating and deflating the body periodically to correspond to the breathing of an individual. The preferred embodiment of the invention also includes a relatively soft cushion on one side of the body for receiving the head of an individual thereon as well as an electric heating pad on top of the cushion and means for increasing and/or decreasing the heat in the heating pad. In addition, a pair of spaced apart elongated vibrators are constructed and dimensioned within the pillow to message an individual's neck and shoulders when the individual's head is resting on the cushion as well as means for increasing and/or decreasing the amplitude and/or rate of vibration. An electric cord is included for connecting the pillow to a source of electrical energy for powering the heating pad, the vibrator and the means for inflating and deflating the body. A textile cover contains the pillow and has a zipper on one side thereof for access to the inside of the pillow. Further, the pillow includes a pillow case of satin material with one open side.

The invention will now be described in connection with the accompanying figures wherein like reference numerals have been used to indicate like parts.

DESCRIPTION OF THE PREFERRED EMBODIMENTS OF THE INVENTION

Figure 1:
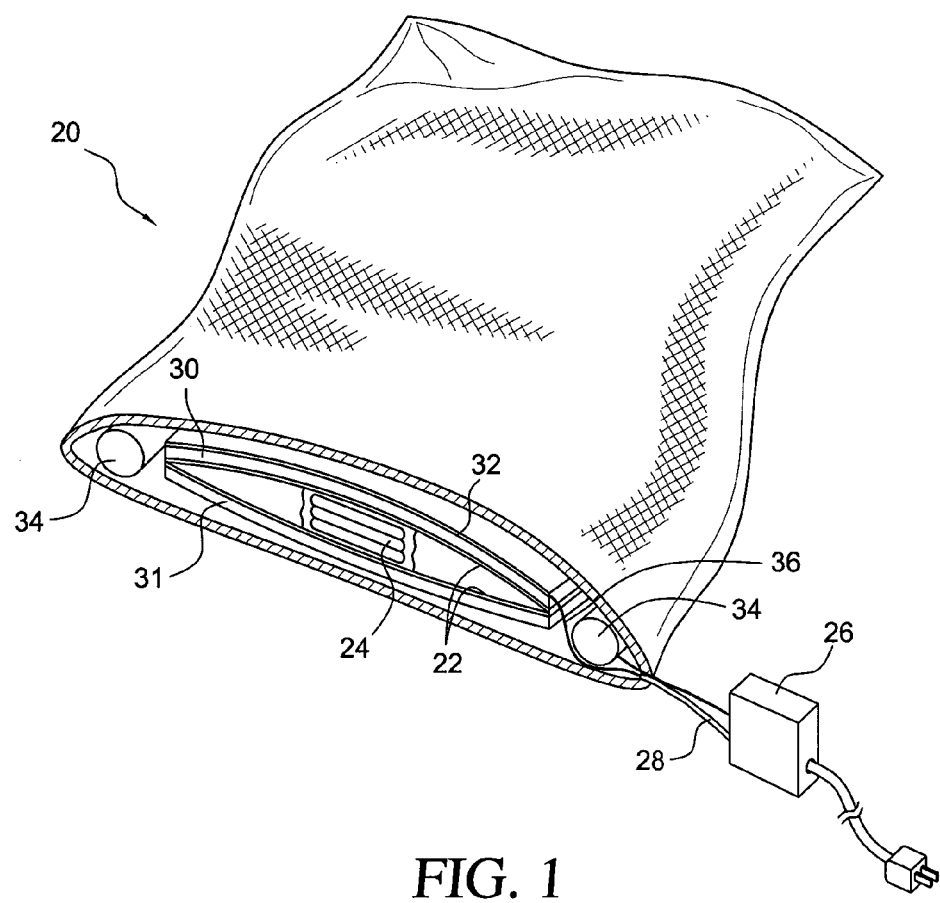
FIG. 1 is a schematic illustration of a pillow in accordance with a preferred embodiment of the invention.

As illustrated in FIG. 1 a pillow 20 includes a pair of relatively impervious panels 22 joined together to form a closed body. This closed body may include a bellows 24 for inflating/deflating with air as controlled by a control mechanism 26 connected to the closed body by a plastic tube 28 of polyvinyl chloride or the like. The control mechanism 26 typically activates a bellows to inflate and deflate the closed body periodically to simulate the respiration of an individual by conventional means as will be well understood by persons of ordinary skill in the art and may include a timer for timing the inflation and deflation for simulating an individual's respiration.

The pillow 20 also includes a relatively soft cushion 30 that may be filled with foam rubber, goose down or other conventional filling with the cushion on top of the upper panel 22. A similar cushion 31 may also be provided on the opposite side of the expandable body. An electric heating pad 32 is provided on top of the cushion 30 and is electrically connected to the control mechanism 26 for increasing or decreasing the heat in the pad 32. The heating pad 32 and heat control 26 are of conventional design or may be of a custom design to fit the specific application as should be well understood of persons of ordinary skill in the art.

A pair of spaced apart elongated vibrators 34 are disposed within the pillow 20 and are constructed and dimensioned to message an individual's neck and upper shoulders when the individual's head is resting on the pillow. Means such as a conventional electric vibrator with a speed or amplitude control may be provided so that the speed and/or amplitude of an eccentric weight on a vibrator can be controlled as desired.

An electric conductor 36 connects the pillow to a source of electricity for heating the heating pad 32, vibrators and means for inflation/deflation of the bellows 24. An outer textile cover 38 encompasses the pillow 20 and includes a zipper (not shown) on one side thereof for gaining access to the interior of the pillow 20. Finally a pillow case of satin material 40 is preferably used for the comfort of an individual.

Figure 2:
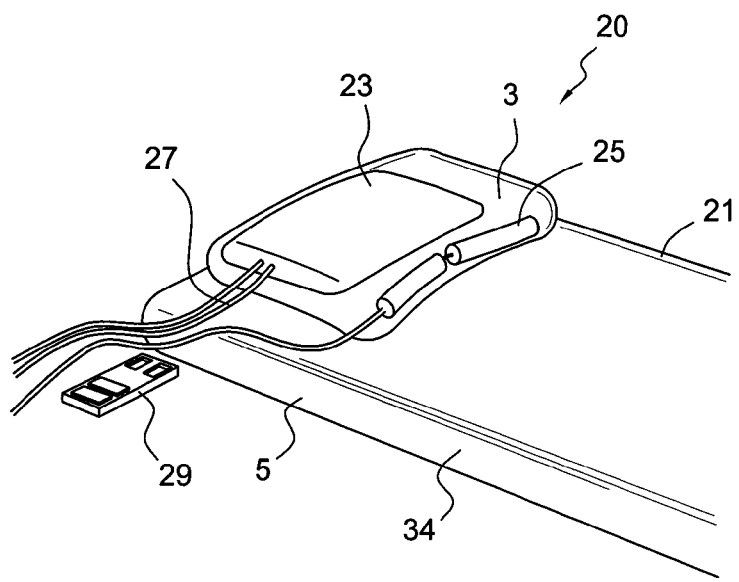
FIG. 2 is a schematic illustration of a pillow in accordance with a preferred embodiment of the invention.
Figure 3:
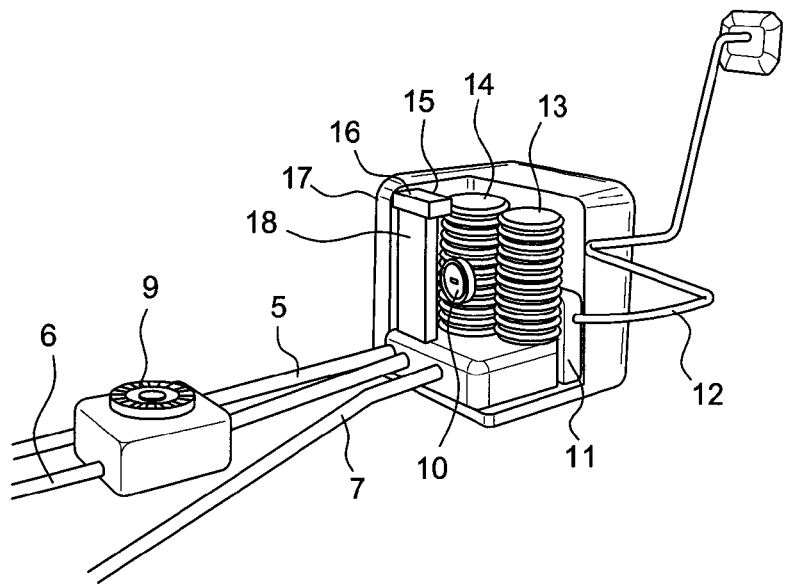
FIG. 3 is a schematic illustration of a device and its internal components along with its control knobs for controlling the inflation and deflation, vibration and heating of the pillow.

As illustrated in FIG. 2, a pillow 20 in accordance with the present invention is disposed on a single bed or cot 21. The pillow preferably is about 60 cm long with the width of about 35 cm and the height of about 10 cm and includes an airbag 23 with a length of about 35 cm by 20 cm width and about a 5 cm height. A neck portion 25 of the pillow 20 having dimensions of about 60 cm by 10 cm by 10 cm includes a pair of cylindrical vibrators 34 each of which have dimensions of about 15 cm by 5 cm by 5 cm. An electric cord 36 with a length about 300 cm connects the vibrators 34 to a conventional electric socket. As shown, a pair of polyvinyl chloride (PVC) tubes 27 having a length of about 300 cm and a width of about 1.5 cm and 1.2 cm respectively provide and air input and an air output for connecting to the bellows 24 (FIG. 1). Further, a remote control 29 may be used to regulate the control 26 (FIG. 1).

The control 26 in accordance with a preferred embodiment of the invention includes an electric cable 5, an air intake tube 6 and an air output tube 7 and an air pressure regulator 9. The control 26 also includes an air temperature controller 10, a rechargeable battery 11 and about 200 cm of electrical wire 12. The control 26 further includes a heater unit 13 for regulating the temperature of the heating pad 32 (FIG. 1), an air pump 14 for filling the bellows 24 (FIG. 1) and an air pressure release button 15. In addition, the control 26 includes an on/off switch 16, a light indicator 17 for indicating that the power is on and a generator 18 voltage regulator for controlling the rate of inflation/deflation, vibration and heating of the pillow.

While the invention has been described in connection with its preferred embodiments it should be recognized that changes and modifications may be made therein without departing from the scope of the appended claims.

What is claimed is:

1. A generally rectangular shaped pillow with a mechanism for simulated respiration consisting of:

a pair of impervious panels having two elongated sides and two short sides joined together to form a generally rectangular shaped enclosed body having two opposite sides, and a bellows and an air pump for filling said bellows, an air pressure release button, a control mechanism consisting of an on/off switch, a light indication for indicating that the power is on and a regulator for controlling the rate of inflation/deflation, and a timer for inflating and deflating said body periodically to correspond to a person's breathing and two relatively soft foam rubber cushions with one of said cushions on each of said two opposite sides of said enclosed body, a plastic tube and wherein said control mechanism is connected to said enclosed body by said plastic tube;

an electric heating pad on top of one of said cushions and a heater unit for increasing/decreasing the heat in said heating pad, a pair of spaced apart elongated vibrators constructed and dimensioned with said pillow to massage an individual's neck and shoulder with the individual's head resting on one of said cushions and means for increasing/decreasing the amplitude or rate of vibration of said vibrators;

a source of electricity and an electric cord connecting said pillow to said source of electricity for heating said heating pad, powering said vibrators and for inflating/deflating said body, a remote controller for remotely controlling said control mechanism and, a textile cover including two elongated sides and two short sides and having a zipper on one side thereof for access to the interior of said pillow, and a pillow case of satin material with one open side for removal of said pillow from said pillow case.

* * * * *